United States Patent [19]

Schlüsener

[11] 4,155,897

[45] May 22, 1979

[54] COMPOSITIONS EXHIBITING CONTROLLED RELEASE PROPERTIES

[75] Inventor: Erwin Schlüsener, Amselweg, Fed. Rep. of Germany

[73] Assignee: Akzona Incorporated, Asheville, N.C.

[21] Appl. No.: 801,935

[22] Filed: May 31, 1977

[30] Foreign Application Priority Data

May 31, 1976 [DE] Fed. Rep. of Germany ....... 2624289

[51] Int. Cl.² ........................... C08K 7/16; C08K 7/18
[52] U.S. Cl. .................... 260/40 R; 260/842; 260/862; 239/60; 424/19; 424/22
[58] Field of Search .................... 260/40 R, 873, 842, 260/862; 239/6, 60; 424/19, 22; 252/252

[56] References Cited

U.S. PATENT DOCUMENTS

| | | | |
|---|---|---|---|
| 2,806,509 | 9/1957 | Bozzacco et al. | 260/40 R |
| 3,036,928 | 5/1962 | Poole | 260/40 R |
| 3,228,897 | 1/1966 | Nellessen | 260/40 R |
| 3,230,184 | 1/1966 | Alford | 260/40 R |
| 3,608,062 | 9/1971 | Krefeld et al. | 239/60 |
| 3,655,129 | 4/1972 | Seiner | 239/60 |
| 3,873,475 | 3/1975 | Pechacek et al. | 260/40 R |
| 4,043,988 | 8/1977 | Cooke et al. | 260/873 |

*Primary Examiner*—Sandra M. Person
*Attorney, Agent, or Firm*—Francis W. Young; Robert F. Green

[57] ABSTRACT

Compositions exhibiting controlled release of an active substance are disclosed. The compositions comprise an unsaturated polyester resin, an active substance, and hollow microspheres of an organic material, an inorganic material, or a mixture thereof.

6 Claims, No Drawings

COMPOSITIONS EXHIBITING CONTROLLED RELEASE PROPERTIES

BACKGROUND OF THE INVENTION

This invention relates to compositions which exhibit controlled release properties and a process for making the same.

The controlled release of active substances in accordance with the present invention is attributable to the gas deposit effect of the instant compositions. The term "gas deposit effect" as used in this application refers to the essentially uniform evaporation of an active substance from a composition, such as a molded article of unsaturated polyester resin, over a long period of time whereby a useful concentration of the active substance may be maintained in the ambient air over a prolonged period of time.

The term "active substance" as used in this application refers to any composition which has a finite vapor pressure at room temperature and which exhibits some useful property when present at some minimum concentration in ambient air. Included in the category of active substances are perfumes, deodorants and insecticides, and the like.

Molded articles which exhibit gas deposit effect are discussed in German Patent Disclosure No. 1,694,240. Such articles, which may be in the form of slabs, spheres, ribbons, tablets, or bars and which are based upon O, O-dimethyl-O-(2,2-dichlorovinyl)-phosphoric acid esters and unsaturated polyester in conjunction with vinyl compounds which are polymerizable therewith, accomplish the gas deposit effect by including in the molded articles, solid filling materials, optionally in conjunction with liquid filling materials, while the weight ratio of active substance to unsaturated polyester is from about 1:4 to about 2:1. The disclosed filling materials include fibers of glass, sisal, hemp, nettle, coir, flax and other vegetable products and synthetic fibers.

It is also known that solid filling materials may be utilized which are mineral in nature, such as titanium oxide, iron oxide, kaolin, quartz, and other inert materials. Liquid filling materials which are suitable for the mentioned purpose are compositions which have a carrier effect, such as dioctyl phthalate, chloroparaffin, and alkyl sulfonic acid arylester.

German Patent Disclosure No. 1,230,259 describes formed masses which exhibit long-lasting insecticidal effect and which are characterized by the combination of a volatile, organic phosphorous compound of a given composition useful as an insecticide, and a thermoplastic, water-insoluble, macromolecular substance such as polyvinyl chloride or mixed polymers containing vinyl chloride. Thus, the absorptivity of the polyvinyl chloride for the active insecticidal substances is limited. If the polyvinyl chloride masses are to be capable of absorbing sufficient insecticide, the corresponding mixtures have to be provided with considerable quantities of softening agents. If insufficient softening agent is present, the content of active substances in the surface of the molded articles declines very rapidly, a limited amount active substance migrates from the interior of the molded articles, and the mass quickly becomes ineffective.

The "cage effect," as a result of which the active substance diffuses only slowly from the deeper layers to the surface, exists to a large extent in the case of duroplastic molded articles, which contain no filling material. Molded articles of duroplastic materials, which contain solid filling materials, as described in German Patent Disclosure No. 1,694,240, in particular in the form of fibers, display a relatively uniform release of the active substance to the surroundings, in a concentration that is effective, and the release takes place over an adequately long period of time. As is also customary and required in the case of unsaturated polyester resins when fibers are to be introduced for reinforcement purposes in the form of non-wovens or fabrics, the fibers have to be free from alkali and provided with a finish for adhesion improvement. The manufacture of the molded articles provided with non-wovens or fabrics made of fibers is relatively expensive. In addition, the fibrous non-wovens or fabrics cannot be added in any desired small increment.

Thus, an object of the present invention is the preparation of molded articles which exhibit gas deposit effect, through the copolymerization of unsaturated polyesters with vinyl compounds polymerized therewith, in the presence of an active substance and at least one solid filling material, with substantially reduced costs and without loss of effectiveness.

SUMMARY OF THE INVENTION

The foregoing and other objects are achieved by the compositions of the present invention which comprise from about 1 to about 60 weight percent of an active substance, from about 98 to about 40 weight percent of an unsaturated polyester resin, and from about 0.2 to about 30 weight percent of hollow microspheres of an organic material, an inorganic material, or a mixture thereof, having an average particle size from about 0.1 microns to about 300 microns and a density from about 0.03 to about 0.7. g/cc.

DESCRIPTION OF THE PREFERRED EMBODIMENTS

The hollow microspheres which are useful in the present invention may be made of any organic or inorganic material. Usually the hollow microspheres are comprised of glass, sodium borosilicate, phenolic resins, or of vinylidene chloride/acrylonitrile copolymers which are commercially available under varied brand-name designations. Such commercially available hollow microspheres are described in the company publications "OClG" of Philadelphia Quartz Company, and in the "Technical Reports" of "Dow Chemical Europe."

The hollow microspheres may range in size from about 0.1 microns to about 300 microns and have wall thicknesses from about 0.02 microns to about 0.1 microns. The microspheres usually have densities from about 0.03 g/cc to about 0.7 g/cc. In the case of hollow microspheres of vinylidene chloride/acrylonitrile, the density is usually about 0.03 g/cc, the particle diameter is on the average about 30 microns and the wall thickness is about 400 to about 500 Angstroms.

Since, in keeping with the process pursuant to the invention, a relatively small quantity of hollow microspheres has to be mixed with the unsaturated polyester together with any other desirable additive, such as hardeners, stabilizers and polymerization accelerators, as well as the active substance, the manufacturing process is greatly simplified and thus has economic advantages. The hollow microspheres may be added in very finely graded quantities and uniformly distributed in the resin. It is also possible to prepare intermediate products of relatively large volume, which may subsequently be reduced to their finally desired form through a mechanical treatment such as sawing.

Among the hollow microspheres of inorganic material those made of glass are preferred, because hollow microspheres made of glass are very much simpler to manufacture, and therefore also more easily accessible, than those of sodium borosilicate. Among the hollow microspheres of organic material, those of vinylidene chloride/acrylonitrile copolymers are especially preferred. Such hollow microspheres excel above all through the fact that they are fully effective with the addition of very small weight constituents. Thus, such hollow microspheres are preferably added in quantities of only 0.4 to 4% by weight, whereby it must be taken into consideration that, in keeping with the quantity added, the gas deposit effect can be very accurately controlled. Hollow microspheres of other materials are usually utilized in quantities of 5 to 30% by weight in order to achieve a full and long-time period of effectiveness.

With respect to the active substances, in addition to pure compounds there may be used in combination an active ingredient and a carrier therefor. Thus, volatile oils may be used as active substances, perhaps with the addition of carrier materials to guarantee a good distribution in the ambient air. Suitable alcohols and propellant gases (fluorocarbons) may be used as carrier materials. Substances with excellent insecticidal effect may be mixed in with the molded articles, for example the O,O-dimethyl-O-(2,2-dichlorovinyl-,)-phosphoric acid ester (DDVP) mentioned in German Patent Disclosure No. 1,694,240. Furthermore, a long-time effectiveness of tear gas may be maintained in rooms by the admixture of $\omega$-bromacetophenone.

Compared with the products filled with fiber mats pursuant to German Patent Disclosure No. 1,694,240, the mechanical strength of which is also improved by means of the fibrous insert and which therefore cannot be processed as easily by mechanical means, the molded articles pursuant to the present invention display only the strength characteristics possessed by the unsaturated polyesters. In part, due to the addition of the hollow microspheres, which may have a lower density, the strength even declines to some extent. On the other hand, the molded articles made pursuant to the invention excel through high stiffness and impact strength. However, the reduction in strength is not a disadvantage, since customarily high demands as to mechanical strength are not usually made on molded articles which exhibit gas deposit effect. In the mechanical division of semi-finished products of large volume, the lower strength is even an advantage. If, however, higher demands are made upon the strength, it is, pursuant to the invention, possible to place a reinforcement in the molded article in any known manner. Fabrics, or nonwovens made of fibers, as well as reinforcing filler materials such as wollastonite, may serve as a reinforcing material.

In this application, the term "unsaturated polyester resins" is used to identify mixtures of unsaturated polyesters and one or more monomers which contain one or more $CH_2=C<$ groups, such as e.g. styrene, vinyl toluene, methyl methacrylate, diallyl phthalate and divinyl benzene. The ratio of monomer to unsaturated polyester in the unsaturated polyester resin is generally 30–50% by weight of monomer to 70–50% by weight of polyester.

Any unsaturated polyester resin may be used in the present invention and may be made by well-known techniques. The unsaturated polyester may, for example, be obtained by reaction of approximately equivalent amounts of a polyhydric alcohol such as ethylene glycol, propylene glycol, diethylene glycol and an unsaturated dibasic carboxylic acid such as maleic acid, fumaric acid, itaconic acid or the related anhydrides in the presence, if desired, of a saturated polycarboxylic acid such as phthalic acid, isophthalic acid, tetrachlorophthalic acid, malonic acid, adipinic acid, succinic acid, sebacic acid and the like.

In order to prepare the molded articles of unsaturated polyesters with gas deposit effect, an unsaturated polyester resin containing vinyl compounds polymerizable therewith may be mixed with an active substance and filling materials, and cured at room temperature. Thus, curing may be carried out according to the methods customarily used for the processing of unsaturated polyester resins by means of an organic peroxide and a polymerization accelerator. In the following Examples use is made of the curing system cumol hydroperoxide/vanadium accelerator, while "Promotor BS" is used as promoter. The active substance employed is a 50% aqueous dispersion of DDVP. The promoter reinforces the curing system and is used in the Examples in order to make up for the inhibiting effect of the water on the curing system, which water is introduced into the polyermization system with the active substance. Such promoters are known and are customarily used with unsaturated polyester resins. Some of them consist of mixtures of numerous substances, as for example the "Promotor BS" which is used. Thioglycolic acid may also successfully be used as a promoter; it is effective to approximately the same extent as the "Promotor BS" that is used.

In the following Examples the basic mixture comprises:

100 parts by weight unsaturated polyester resin
80 parts by weight DDVP - 50% aqueous dispersion
3 parts by weight cumol hydroperoxide
2 parts by weight vanadium accelerator
1 part by weight Promotor BS.

The release of gas by the molded item is measured by a period of up to about half a year, referred to the original weight of the molded item, whereby it is found that there exist three characteristic gas release velocity ranges. In all experiments one may determine a relatively high gas release velocity during the first week, which then drops to a distinctly lower level for a period of about three weeks, whereupon it again declines and then remains largely constant for several weeks. It is desirable that the gas release velocity during the first phase remain as low as possible and that the velocities in the second and third phase should be as close to one another as possible, so that an effectiveness of longer duration will be achieved. The results of Examples 1–12 are summarized in Table I.

TABLE I

| Filling material addition | Example 1 | 2 | 3 | 4 | 5 | 6 | 7 | 8 | 9 | 10 | 11 | 12 |
|---|---|---|---|---|---|---|---|---|---|---|---|---|
| Hollow microspheres of | | | | | | | | | | | | |
| vinylidene chloride/acrylonitrile copolymer | — | — | 0.5% | 0.5% | 1.5% | 1.5% | 3.0% | 3.0% | 1.5% | 1.5% | — | — |
| phenolic resin | — | — | — | — | — | — | — | — | — | — | 30% | 30% |
| Dioctyl phthalate | — | — | — | — | — | — | — | — | 20% | 20% | — | — |
| Glass fiber non-woven | — | 25% | — | 25% | — | 25% | — | 25% | — | 25% | — | 25% |
| Gas release velocity in percent per week | | | | | | | | | | | | |
| 1st week | 7.7 | 4.4 | 4.0 | 3.6 | 3.9 | 2.9 | 5.0 | 2.7 | 4.9 | 4.3 | 4.4 | 2.6 |
| up to the 4th week | 1.3 | 1.2 | 1.3 | 1.1 | 1.1 | 1.0 | 1.3 | 0.8 | 1.4 | 1.1 | 0.9 | 0.6 |
| after the 4th week | 0.25 | 0.5 | 0.5 | 0.5 | 0.4 | 0.4 | 0.5 | 0.4 | 0.5 | 0.4 | 0.4 | 0.4 |

From the foregoing Table I, it is evident that in the case of molded articles of unfilled unsaturated polyesters, there is a very high level of gas release during the first week. Up to the fourth week this is followed by a relatively high release velocity level, which then declines very rapidly to a very low level. Here, the known cage effect is then encountered and the molded article has reached its limit of effectiveness after little more than 4 weeks (Example 1). The gas release velocity, which after 4 weeks has dropped to 0.25% per week, continues to decline strongly and is no longer sufficient to release an adequate quantity of active substance to the ambient air.

In contrast, during the first week, the gas release velocity of molded articles with gas deposit effect that have been filled with glass fiber mats has been reduced to about half, which makes possible a longer total duration of effectiveness (Example 2). Even after 10 to 12 weeks, the gas release velocity is still on the same level as after 4 weeks.

The additional examples then show that, in the case of the molded articles made pursuant to the invention, the gas release velocity has been made more uniform at least to the same extent, or even more favorably. Such an advantage is achieved with a very small quantity of hollow microspheres, which is shown by the data in Table I.

Analogous gas release velocities may likewise be found with the other active substances used in an analogous manner with the molded articles with gas deposit effect pursuant to the invention, which are given off to the ambient air, where they take effect. For example, a perfuming effect of long duration may be achieved with a molded article provided with lemon oil pursuant to the invention. It is assumed that, in the case of the molded articles pursuant to the invention, the diffusion of the active substances is controlled through the addition of hollow microspheres, and that in this manner one arrives at the characteristic of releasing the readily volatile active substance to the ambient atmosphere in an effective quantity for several months.

What is claimed is:

1. A composition which when cured is capable of exhibiting controlled release of an active substance which has a finite vapor pressure at room temperature and which exhibits some useful property when present at some minimum concentration in the ambient air, comprising from about 1 to about 60 weight percent of the active substance, from about 98 to about 40 weight percent of an unsaturated polyester resin comprising a mixture of unsaturated polyester and one or more monomers which contain one or more $CH_2=C<$ groups, and from about 0.2 to about 30 weight percent of hollow microspheres of an organic material, an inorganic material or a mixture thereof, having an average particle diameter from about 0.1 to about 300 microns and a density from about 0.03 to about 0.7 grams/cc.

2. The composition of claim 1 in which the hollow microspheres are present at a weight percentage of from about 0.4 to about 4 percent, are comprised of vinylidene chloride/acrylonitrile, have a density of about 0.03 g/cc and have a wall thickness from about 400 to about 500 Angstroms.

3. The composition of claim 2 in which the active substance is selected from the group consisting of perfumes, deodorants, and insecticides.

4. A composition capable of exhibiting controlled release of an active substance which has a finite vapor pressure at room temperature and which exhibits some useful property when present at some minimum concentration in ambient air, comprising from about 98 to about 40 weight percent of an unsaturated polyester resin comprising a mixture of unsaturated polyester and one or more monomers which contain one or more $CH_2=C<$ groups, which has been cured in the presence from about 1 to about 60 weight percent of the active substance and from about 0.2 to about 30 weight percent of hollow microspheres of an organic material, an inorganic material or a mixture thereof, having an average particle size from about 0.1 to about 300 microns and a density from about 0.03 to about 0.7 grams/cc.

5. The composition of claim 4 in which the hollow microspheres are present at a weight percentage of from about 0.4 to about 4 percent, are comprised of vinylidene chloride/acrylonitrile, have a density of about 0.03 grams/cc and have a wall thickness of from about 400 to about 500 Angstroms.

6. The composition of claim 5 in which the active substance is selected from the group consisting of perfumes, deodorants, and insecticides.

* * * * *